US00PP22011P2

(12) United States Plant Patent
Valenzuela et al.

(10) Patent No.: US PP22,011 P2
(45) Date of Patent: Jul. 5, 2011

(54) ***LIMONIUM* PLANT NAMED 'JSAHTI'**

(50) Latin Name: *Limonium sinense*
Varietal Denomination: Jsahti

(75) Inventors: Camilo Herrera Valenzuela, Bogotá (CO); Camilo Alejandro Chivatá Romero, Bogotá (CO)

(73) Assignee: C.I. Valmar S.A., Bogotá (CO)

( * ) Notice: Subject to any disclaimer, the term of this patent is extended or adjusted under 35 U.S.C. 154(b) by 0 days.

(21) Appl. No.: 12/653,959

(22) Filed: Dec. 21, 2009

(51) Int. Cl.
*A01H 5/00* (2006.01)

(52) U.S. Cl. ..... Plt./358

(58) Field of Classification Search ..... Plt./449, Plt./358

See application file for complete search history.

*Primary Examiner* — June Hwu
(74) *Attorney, Agent, or Firm* — C. A. Whealy

(57) ABSTRACT

A new and distinct cultivar of *Limonium* plant named 'Jsahti', characterized by its erect, strong and medium in length flowering stems; freely flowering habit; short flowering cycle; relatively small flowers with white-colored persistent calyces; and excellent postproduction longevity.

1 Drawing Sheet

Botanical designation: *Limonium sinense.*
Cultivar denomination: 'JSAHTI'.

BACKGROUND OF THE INVENTION

The present invention relates to a new and distinct cultivar of *Limonium* plant, botanically known as *Limonium sinense*, commercially used as a cut flower *Limonium*, and hereinafter referred to by the name 'Jsahti'.

The new *Limonium* plant is a product of a planned breeding program in Madrid, Cundinamarca, Colombia. The objective of the breeding program is to create new high-yielding *Limonium* cultivars that have a short forcing cycle and that are resistant to pathogens.

The new *Limonium* plant originated from an open-pollination in Madrid, Cundinamarca, Colombia in December, 2004 of a proprietary selection of *Limonium sinense* identified as code number JS 401001-3, not patented, as the female, or seed, parent with an unknown selection of *Limonium sinense* as the male, or seed, parent. The new *Limonium* plant was discovered and selected by the Inventors as a single flowering plant from within the progeny of the stated open-pollination grown in a controlled environment in Madrid, Cundinamarca, Colombia on Jul. 4, 2005.

Asexual reproduction of the new *Limonium* plant since February, 2006 by tissue culture in a controlled environment in Madrid, Cundinamarca, Colombia has shown that the unique features of this new *Limonium* plant are stable and reproduced true to type in successive generations.

SUMMARY OF THE INVENTION

Plants of the new *Limonium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Jsahti'. These characteristics in combination distinguish 'Jsahti' as a new and distinct cultivar of *Limonium* plant:

1. Erect, strong and medium in length flowering stems.
2. Freely flowering habit.
3. Short flowering cycle.
4. Relatively small flowers with white-colored persistent calyces.
5. Excellent postproduction longevity.

Plants of the new *Limonium* can be compared to plants of the female parent selection. Plants of the new *Limonium* differ primarily from plants of the female parent selection in yield as plants of the new *Limonium* produce more flowering stems than plants of the female parent selection. In addition, plants of the new *Limonium* and the female parent selection differ in flower color.

Plants of the new *Limonium* can be compared to plants of *Limonium sinense* 'Silver Diamond', not patented. In side-by-side comparisons conducted in Madrid, Cundinamarca, Colombia, plants of the new *Limonium* differed primarily from plants of 'Silver Diamond' in the following characteristics:

1. Plants of the new *Limonium* had shorter flowering stems than plants of 'Silver Diamond'.
2. Plants of the new *Limonium* were more freely flowering than plants of 'Silver Diamond'.
3. Plants of the new *Limonium* had smaller flowers than plants of 'Silver Diamond'.
4. Plants of the new *Limonium* had a shorter flowering cycle than plants of 'Silver Diamond'.

BRIEF DESCRIPTION OF THE PHOTOGRAPHS

The accompanying colored photographs illustrate the overall appearance of the new *Limonium* plant, showing the colors as true as it is reasonably possible to obtain in colored reproductions of this type. Colors in the photographs may differ slightly from the color values cited in the detailed botanical description which accurately describe the colors of the new *Limonium* plant.

The photograph at the top of the sheet comprises a side perspective view of a typical flowering stem of 'Jsahti'.

The photograph at the bottom of the sheet is a close-up view of typical inflorescences of 'Jsahti'.

DETAILED BOTANICAL DESCRIPTION

The aforementioned photographs and following observations and measurements describe plants of the new *Limonium* grown in Madrid, Cundinamarca, Colombia in a polyethylene-covered greenhouse in ground beds. During the production of the plants, day temperatures ranged from 15° C. to 25° C., night temperatures ranged from 8° C. to 12° C. and light levels averaged 21.4 KWH/$m^2$. Plants were pinched one time about six weeks after planting. Plants were 17 weeks old when the photographs and description were taken. Color references are made to The Royal Horticultural Society Colour Chart, 2007 Edition, except where general terms of ordinary dictionary significance are used.

Botanical classification: *Limonium sinense* 'Jsahti'.

Parentage:

*Female, or seed, parent.*—Proprietary selection of *Limonium sinense* identified as code number JS 401001-3, not patented.

*Male, or pollen, parent.*—Unknown selection of *Limonium sinense*, not patented.

Propagation:

*Type.*—By tissue culture.

*Time to initiate roots.*—About twelve days with day temperatures ranging from 15° C. to 25° C. and night temperatures ranging from 8° C. to 12° C.

*Time to produce a rooted young plant.*—About four weeks with day temperatures ranging from 15° C. to 25° C. and night temperatures ranging from 8° C. to 12° C.

*Root description.*—Fleshy; medium in thickness; white in color.

*Rooting habit.*—Freely branching; dense.

Plant description:

*Appearance.*—Perennial subshrub grown as a cut flower; erect, strong and medium in length flowering stems; inverted broad triangle form; leaves basal; freely flowering habit; numerous flowers arranged in symmetrical panicles; vigorous growth habit.

*Branching habit.*—Freely branching habit; after pinching, about 15 to 18 flowering stems develop per plant.

*Flowering stems.*—Length: About 72 cm. Spread: About 30 cm by 34 cm. Diameter: About 2.5 mm. Internode length: About 5.5 cm. Aspect: Very erect. Strength: Strong. Texture: Smooth, glabrous; longitudinally ridged. Color: Close to 146B.

Foliage description:

*Arrangement.*—Alternate, simple; sessile, clasping.

*Length.*—About 22 cm to 32 cm.

*Width.*—Towards the apex, about 4.2 cm to 6.5 cm; towards the base, close to 0.8 cm.

*Shape.*—Elongated spatulate.

*Apex.*—Rounded.

*Base.*—Attenuate.

*Margin.*—Entire to slightly sinuate.

*Texture, upper and lower surfaces.*—Smooth, glabrous.

*Venation pattern.*—Pinnate; arcuate.

*Color.*—Developing leaves, upper surface: Close to 146A. Developing leaves, lower surface: Close to 147B. Fully expanded leaves, upper surface: Close to 146B; towards the base, close to 146D; venation, close to 147B.

*Fully expanded leaves, lower surface.*—Close to 147B; towards the base, close to 145C; venation, close to 145D.

Flower description:

*Flower arrangement and habit.*—Outwardly arching, branching and pyramidal in shape panicles with numerous flowers; flowers actinomorphic and symmetrical; freely flowering habit, about 1,400 flowers per flowering stem; flowers face mostly upright; flowers sessile.

*Flowering response.*—In Colombia, plants flower year round; early flowering response, plants begin flowering about 17 weeks after planting; short flowering cycle.

*Post-production longevity.*—As a cut flower, flowers last for about 20 to 30 days; corolla not persistent, calyx persistent.

*Fragrance.*—Mildly fragrant, sweet.

*Inflorescence height.*—About 62 cm.

*Inflorescence diameter.*—About 15 cm by 24 cm.

*Flower diameter.*—About 5 mm.

*Flower depth (height).*—About 9 mm.

*Flower buds.*—Length: About 7 mm. Diameter: About 2.5 mm. Shape: Fusiform, pointed oval. Color: Close to NN155D.

*Corolla.*—Petals per flower: Five in a single whorl. Petal length: About 1.1 cm. Petal width: About 2 mm. Petal shape: Ligulate. Petal apex: Emarginate. Petal base: Attenuate. Petal margin: Entire. Petal texture, upper and lower surfaces: Smooth, glabrous; satiny, membraneous. Petal color: When opening, upper and lower surfaces: Close to 3B. Fully opened, upper and lower surfaces: Towards the apex, close to 3B; midsection and base, close to NN155D.

*Calyx.*—Sepals per flower: Five in a single whorl; calyx narrowly funnelform. Sepal length: About 7 mm. Sepal diameter: About 2 mm. Sepal shape: Deltoid. Sepal apex: Erose. Sepal base: Fused. Sepal margin: Entire to erose. Sepal texture, upper and lower surfaces: Smooth, glabrous; papery. Sepal color: When opening and fully opened, upper surface: Close to NN155D. When opening and fully opened, lower surface: Close to NN155D.

*Flower bracts.*—Quantity per flower: One. Length: About 4 mm. Width: About 2 mm. Color, upper and lower surfaces: Close to 146B.

*Peduncles.*—Length: About 9.5 cm. Diameter: About 3 mm. Strength: Strong. Angle: About 45° from stem axis. Texture: Smooth, glabrous; longitudinally ridged. Color: Close to 147A.

*Reproductive organs.*—Androecium: Stamen number: Five per flower. Filament length: About 5 mm. Filament color: Close to NN155D. Anther length: Less than 1 mm. Anther shape: Oval. Anther color: Close to 1B. Amount of pollen: Scarce. Pollen color: Close to 1C. Gynoecium: Pistil number: One per flower. Pistil length: About 8 mm. Style length: About 4 mm. Style color: Close to NN155D. Stigma shape: Capitate, filiform. Stigma color: Close to 1C. Ovary color: Close to 145D.

*Seeds/fruits.*—Seed and fruit development have not been observed.

Disease/pest resistance: Plants of the new *Limonium* have not been observed to be resistant to pathogens and pests common to *Limonium*.

Temperature tolerance: Plants of the new *Limonium* have been observed to tolerate temperatures from about −1° C. to about 30° C.

It is claimed:

1. A new and distinct *Limonium* plant named 'Jsahti' as illustrated and described.

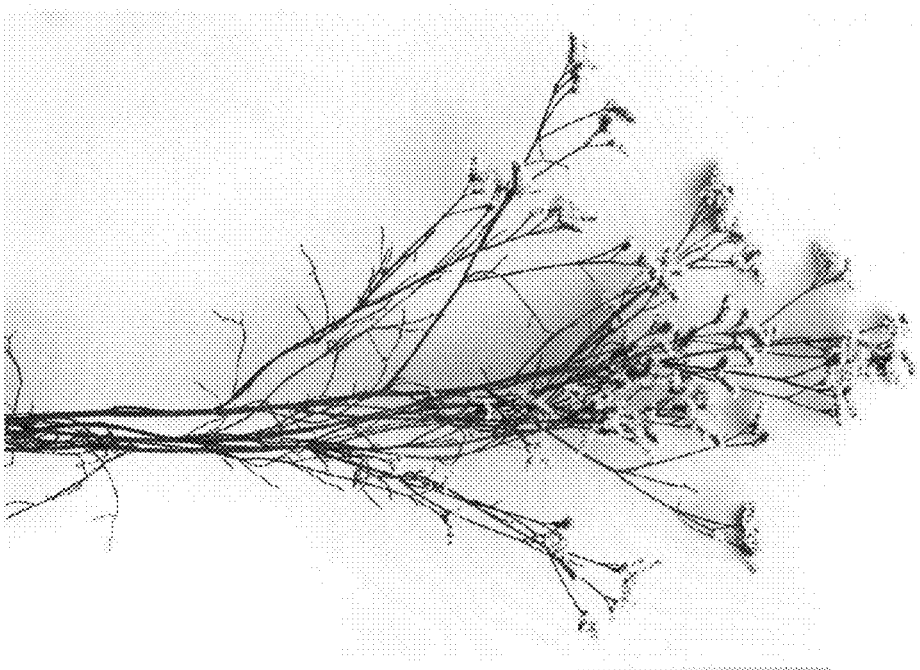
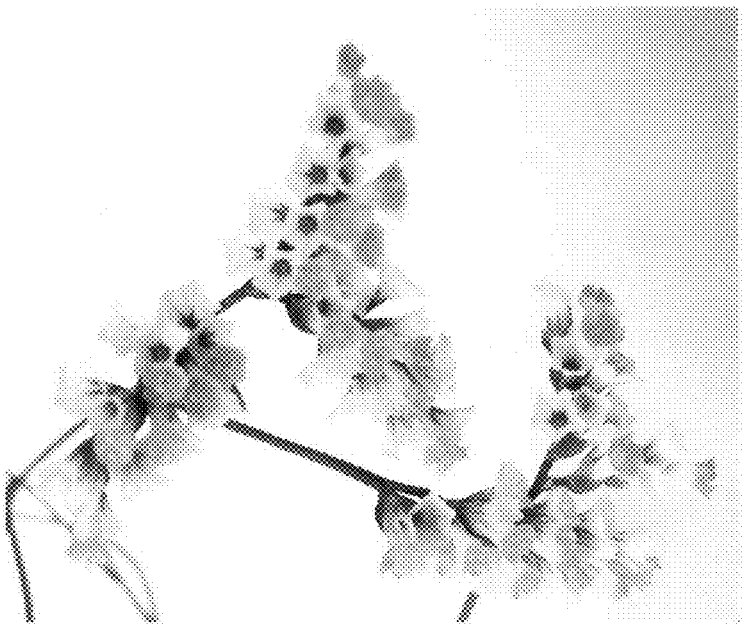

* * * * *